United States Patent [19]

Black et al.

[11] Patent Number: 5,409,944
[45] Date of Patent: Apr. 25, 1995

[54] ALKANESULFONAMIDO-1-INDANONE DERIVATIVES AS INHIBITORS OF CYCLOOXYGENASE

[75] Inventors: W. Cameron Black, Pointe-Claire; Chun-Sing Li, Dollard Des Ormeaux; Daniel Guay, Notre Dame de L'lle Perrot; Petpiboon Prasit, Kirkland; Patrick Roy, Dollard Des Ormeaux, all of Canada

[73] Assignee: Merck Frosst Canada, Inc., Kirkland, Canada

[21] Appl. No.: 30,924

[22] Filed: Mar. 12, 1993

[51] Int. Cl.$^6$ .................. C07D 285/13; A61K 31/41
[52] U.S. Cl. .................. 514/359; 514/361; 514/362; 514/363; 514/364; 514/365; 514/369; 514/372; 514/374; 514/384; 514/398; 514/445; 514/471; 548/127; 548/129; 548/135; 548/136; 548/142; 548/144; 548/187; 548/204; 548/213; 548/243; 548/235; 548/259; 548/264.4; 548/324.1; 549/65; 549/479
[58] Field of Search ............... 514/359, 361, 362, 363, 514/364, 365, 369, 372, 374, 384, 398, 444, 471; 548/127, 129, 135, 136, 142, 144, 187, 204, 213, 235, 243, 259, 264.4, 324.1; 549/65, 479

[56] References Cited

U.S. PATENT DOCUMENTS

| | | | |
|---|---|---|---|
| 4,244,960 | 1/1981 | Schroder et al. | 41/263 |
| 4,375,479 | 3/1983 | Schroeder et al. | 424/279 |
| 4,411,910 | 10/1983 | Schroeder et al. | 424/279 |
| 4,696,948 | 9/1987 | Petzoldt | 514/605 |

FOREIGN PATENT DOCUMENTS 61-130870 of 1986 Japan.
2-42997 9/1990 Japan.

*Primary Examiner*—Robert Gerstl
*Attorney, Agent, or Firm*—Curtis C. Panzer; David L. Rose

[57] ABSTRACT

Disclosed are compounds of Formula I useful in the treatment of cyclooxygenase mediated diseases such as pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries.

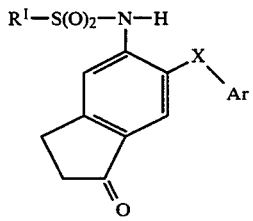

18 Claims, No Drawings

ALKANESULFONAMIDO-1-INDANONE DERIVATIVES AS INHIBITORS OF CYCLOOXYGENASE

BACKGROUND OF THE INVENTION

This invention relates to compounds and pharmaceutical compositions for the treatment of cyclooxygenase mediated diseases and methods of treating thereof.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Up until recently, only one form of cyclooxygenase had been characterized, this corresponding to cyclooxygenase-1 or the constitutive enzyme, as originally identified in bovine seminal vesicles. Recently the gene for an inducible form of cyclooxygenase (cyclooxygenase-2) has been cloned, sequenced and characterized from chicken, murine and human sources. This enzyme is distinct from the cyclooxygenase-1 which has now also been cloned, sequenced and characterized from sheep, murine and human sources. The second form of cyclooxygenase, cyclooxygenase-2, is rapidly and readily inducible by a number of agents including mitogens, endotoxin, hormones, cytokines and growth factors. As prostaglandins have physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties of a conventional non-steroidal antiinflammatory drug (NSAID), and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and a lessened ability to induce asthma attacks in aspirin-sensitive asthmatic subjects.

SUMMARY OF THE INVENTION

The invention encompasses compounds of Formula I

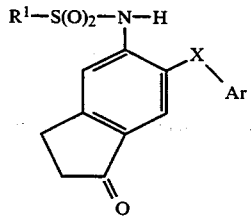

which are useful in the treatment of cyclooxygenase mediated diseases, in particular cyclooxygenase-2 mediated diseases.

The invention also encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of Formula I as described herein.

The invention also encompasses methods of inhibiting cyclooxygenase and treating cyclooxygenase mediated diseases comprising:

administration to a patient in need of such treatment of a non-toxic therapeutically effective amount of a compound of Formula I as disclosed herein.

DETAILED DESCRIPTION OF THE INVENTION

The invention encompasses compounds of Formula I

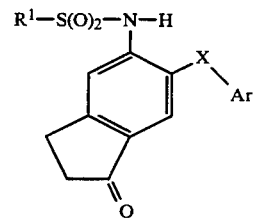

and pharmaceutically acceptable salts thereof wherein:

$R^1$ is selected from the group consisting of
 (a) $C_{1-7}$alkyl, and
 (b) mono-, di-, tri-, tetra- and per-substituted $C_{1-7}$alkyl, wherein the substituent is fluoro;

X is O, S, or —$CH_2$—;

Ar is a mono or disubstituted aromatic ring, said ring selected from
 (a) a ring of 5 atoms containing one O, S or N atom and optionally, 1, 2 or 3 additional N atoms; and
 (b) a ring of 6 atoms containing 2, 3 or 4 nitrogen atoms;

wherein the substituents are independently selected from
 (a) hydrogen,
 (b) $C_{1-7}$alkyl,
 (c) halogen, including F, Cl, Br, and I,
 (d) $OCH_3$,
 (e) $SCH_3$,
 (f) $CF_3$,
 (g) $COCH_3$ and
 (h) $S(O)_2CH_3$.

For purposes of this specification alkyl is defined to include linear, branched or cyclic alkyl including methyl, ethyl, 2-propyl, 1,1-dimethylethyl, cyclopropyl, cyclobutyl, cyclohexyl, and cyclohexyl. Similarly fluorosubstituted alkyl as defined above is defined to include fluoromethyl, trifluoromethyl, 2-fluoroethyl, perfluoroheptyl, perfluorocyclopropyl, and perfluoroheptyl.

One genus of this embodiment concerns compounds of Formula I wherein:

Ar is a mono- or disubstituted aromatic group wherein the aromatic group is selected from the group consisting of
 (1) furanyl,
 (2) diazinyl, triazinyl, tetrazinyl, (3) imidazolyl,
(4) isooxazolyl,
(5) isothiazolyl,
(6) oxadiazolyl,
(7) oxazoly,
(8) pyrazolyl,
(9) pyrrolyl,
(10) thiadiazolyl,
(11) thiazolyl,
(12) thienyl,
(13) triazoly, and
(14) tetrazolyl,
wherein the substituents are independently selected from
(a) hydrogen,
(b) $C_{1-7}$alkyl,
(c) halogen, including F, Cl, Br, and I,
(d) $OCH_3$,
(e) $SCH_3$, and
(f) $CF_3$,
(g) $COCH_3$, and
(h) $S(O)_2CH_3$ In one class of this genus the invention concerns compounds of Formula I wherein,
$R^1$ is selected from the group consisting of
(a) methyl, ethyl, propyl, and butyl
(b) mono, di or tri substituted $C_{1-4}$alkyl, wherein the substituent is fluoro;
X is O, S or $CH_2$
Ar is a mono or disubstituted aromatic group wherein the aromatic group is selected from the group consisting of
(1) 2-furanyl,
(2) 3-furanyl,
(3) 2-thienyl,
(4) 3-thienyl,
(5) 3-isooxazolyl,
(6) 4-isooxazolyl,
(7) 5-isooxazolyl,
(8) 3-isothiazolyl,
(9) 4-isothiazolyl,
(10) 5-isothiazolyl,
(11) 2-oxazolyl,
(12) 4-oxazolyl,
(13) 5-oxazolyl,
(14) 2-thiazolyl,
(15) 4-thiazolyl,
(16) 5-thiazolyl,
(17) 1,2,3-thiadiazol-4-yl,
2(18) 1,2,3-thiadiazol-5-yl,
(19) 1,2,4-thiadiazol-3-yl,
(20) 1,2,4-thiadiazol-5-yl,
(21) 1,3,4-thiadiazol-2-yl,
(22) 1,2,5-thiadiazol- 3-yl,
(23) 1,2,3-oxadiazol-4-yl,
(24) 1,2,3-oxadiazol-5-yl,
(25) 1,2,4-oxadiazol-3-yl,
(26) 1,2,4-oxadiazol-5-yl,
(27) 1,3,4-oxadiazol-2-yl,
(28) 1,2,5-oxadiazol-3-yl,
(29) pyrazol-4-yl,
(30) pyrazol-5-yl,
(31) 1,2,3-triazol-4-yl,
(32) 1,2,3-triazol-5-yl,
(33) 1,2,4-triazol-3-yl,
(34) 1,2,4-triazol-5-yl,
(35) 1,2-diazinyl,
(36) 1,3-diazinyl,
(37) 1,4-diazinyl,
(38) imidazol-2-yl,
(39) imidazol-4-yl,
(40) imidazol-5yl,
(41) tetrazol-5-yl,
wherein the substituents are independently selected from
(a) hydrogen,
(b) $C_{1-3}$alkyl,
(c) halogen, including F, Cl, Br, and I,
(d) $OCH_3$,
(e) $SCH_3$,
(f) $CF_3$,
(g) $COCH_3$, and
(h) $S(O)_2CH_3$ In a second embodiment, de invention encompasses pharmaceutical compositions for inhibiting cyclooxygenase and for treating cyclooxygenase mediated diseases as disclosed herein comprising a pharmaceutically acceptable carrier and a non-toxic therapeutically effective amount of compound of Formula I as described above.

Within this embodiment the invention encompasses pharmaceutical compositions for inhibiting cyclooxygenase-2 and for treating cyclooxygenase-2 mediated diseases as disclosed herein comprising a pharmaceutically acceptable carrier and a non-toxic therapeutically effective amount of compound of Formula I as described above.

In a third embodiment, the invention encompasses a method of inhibiting cyclooxygenase and treating cyclooxygenase mediated diseases as disclosed herein comprising administration to a patient in need of such treatment of a non-toxic therapeutically effective amount of a compound of Formula I as disclosed herein.

Within this embodiment the invention encompasses a method of inhibiting cyclooxygenase-2 and treating cyclooxygenase-2 mediated diseases as disclosed herein comprising administration to a patient in need of such treatment of a non-toxic therapeutically effective amount of a compound of Formula I as disclosed herein.

As disclosed elsewhere in this specification in further detail, these diseases include pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursiris, burns, injuries.

Exemplifying the invention are the following compounds:

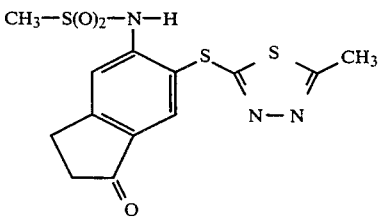

-continued

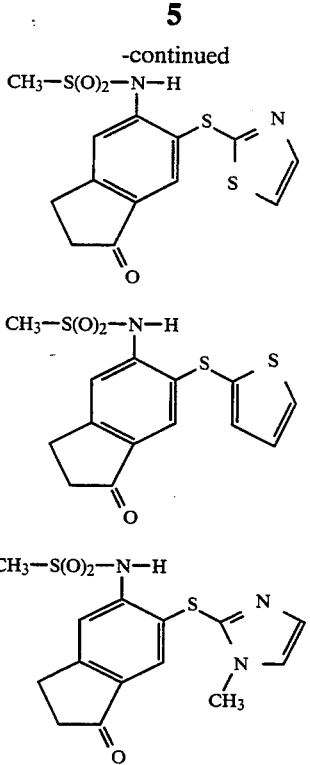

Illustrative of the pharmaceutically acceptable salts is the formula

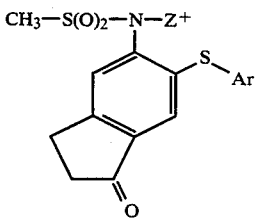

wherein Ar is defined above and Z+ is a pharmaceutically acceptable monovalent counterion. As is well appreciated by those of skill in the art, the pharmaceutically acceptable counterions include, aluminum, calcium, lithium, magnesium, potassium, sodium, barium, zinc, ammonium, or an amino acid such as glycine, alanine, valine, leucine, isoleucine, serine, threonine, aspartic acid, asparagine, glutamic acid, lysine, hydroxylysine, histidine, arginine, phenylalanine, tyrosine, tryptophan, thyroxine, cystine, cysteine, methionine, proline, hydroxyproline, ornithine, β-alanine, α-amino butyric acid, sarcosine, betaine, homoserine, and citrulline, or mono, di, or tri$C_{1-6}$alkylamino.

Compounds of Formula I are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such compounds may inhibit cellular neoplastic transformations and metastic tumor growth and hence can be used in the treatment of cancer. Compounds of Formula I will also inhibit prostanoid-induced smooth muscle contraction by preventing the synthesis of contractile prostanoids and hence may be of use in the treatment of dysmenorrhea, premature labor and asthma.

By virtue of their high cyclooxygenase-2 (COX-2) activity and/or their specificity for cyclooxygenase-2 over cyclooxygenase-1 (COX-1 ), compounds of Formula I will prove useful as alternatives to conventional non-steroidal anti-inflammatory drags (NSAID'S) particularly where such non-steroidal anti-inflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, compounds of Formula I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of compound of Formula I as defined above and one or more ingredients such as another pain reliever including acetaminophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effective amount of compound of Formula I, optionally co-administered with one or more of such ingredients as listed immediately above.

Compounds of the present invention are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ (PGE$_2$) synthesized in the presence of arachidonic acid, cyclooxygenase-1 or cyclooxygenase-2 and a compound of formula I. The IC50 values represent the concentration of inhibitor required to return PGE$_2$ synthesis to 50% of that obtained as compared to the uninhibited control. Illustrating this aspect, we have found that Compounds 1 through 26 are more than 100 times more effective in inhibiting COX-2 than they are at inhibiting COX-1. In addition they all have an IC50 of 1 nM ,to 1 μM. By way of comparison, Ibuprofen has an IC50 for COX-2 of 1 μM, and Indomethacin has an IC50 for COX-2 of approximately 100 nM.

For the treatment of any of these cyclooxygenase mediated diseases compounds of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compounds of the invention are, effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium,, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of Formula (I) are employed. (For purposes of this application, topical application shall include mouth washes and gargles.)

Dosage levels of the order of from about 0.01 mg to about 140 mg per kilogram of body weight per day are useful in the treatment of the above-indicated conditions, or alternatively about 0.5 mg to about 7 g. per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 1000 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Compounds of the instant invention are conveniently prepared using the procedures described in the methods below. Additional relavent chemistry is described in U.S. Pat. No. 4,375,479, issued to Schroeder, et al., Mar. 1, 1983 which is hereby incorporated by reference.

Method A

Indanol I is coupled with an appropriate alkylating agent and then nitrated to give the nitro ether II. Reduction, which can be performed by catalytic hydrogenation, followed by treatment with a sulfonylating agent such as an alkanesulfonyl chloride in the presence of a base like pyridine gives he sulfonamide III. Benzylic oxydation can be accomplished by a variety of reagents such as pyridinium chlorochromate in refluxing benzene to give the alkyl sulfonamido indanone IV.

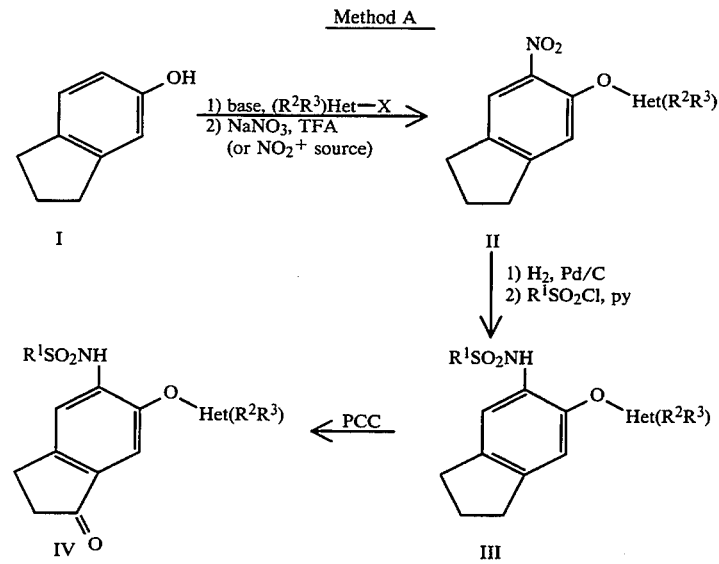

Method B

Amine V is acetylated followed by bromination to give acetylamino bromo indane VI. Oxidation, which can be performed by many reagents such as chromium trioxide in acetic acid, followed by acid hydrolysis gives the amino indanone VII. Conversion of the amino group into a nitro group is done by treatment of the corresponding diazonium salt with sodium nitrite, in the presence of copper. Protection of the carbonyl as a dioxolane provides the bromo nitro ketal VIII. Coupling with an appropriate nucleophile proceeds under basic conditions. Reduction of the nitro group with iron powder with concomitant hydrolysis of the ketal leads to the amino indanone IX. Monosulfonylation gives the alkanesulfonamido indanone X. In cases where monosulfonylation is impractical, the amino indanone IX is converted to the bissulfonamide followed by basic hydrolysis with aqueous hydroxide to give the alkanesulfonamido indanone X.

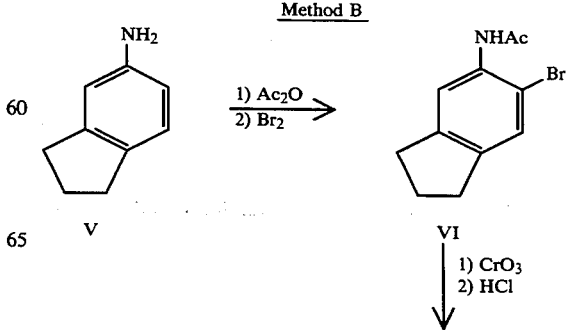

the sulfonamide XII which upon hydrolysis gives the alkanesulfonamido indanone XIII.

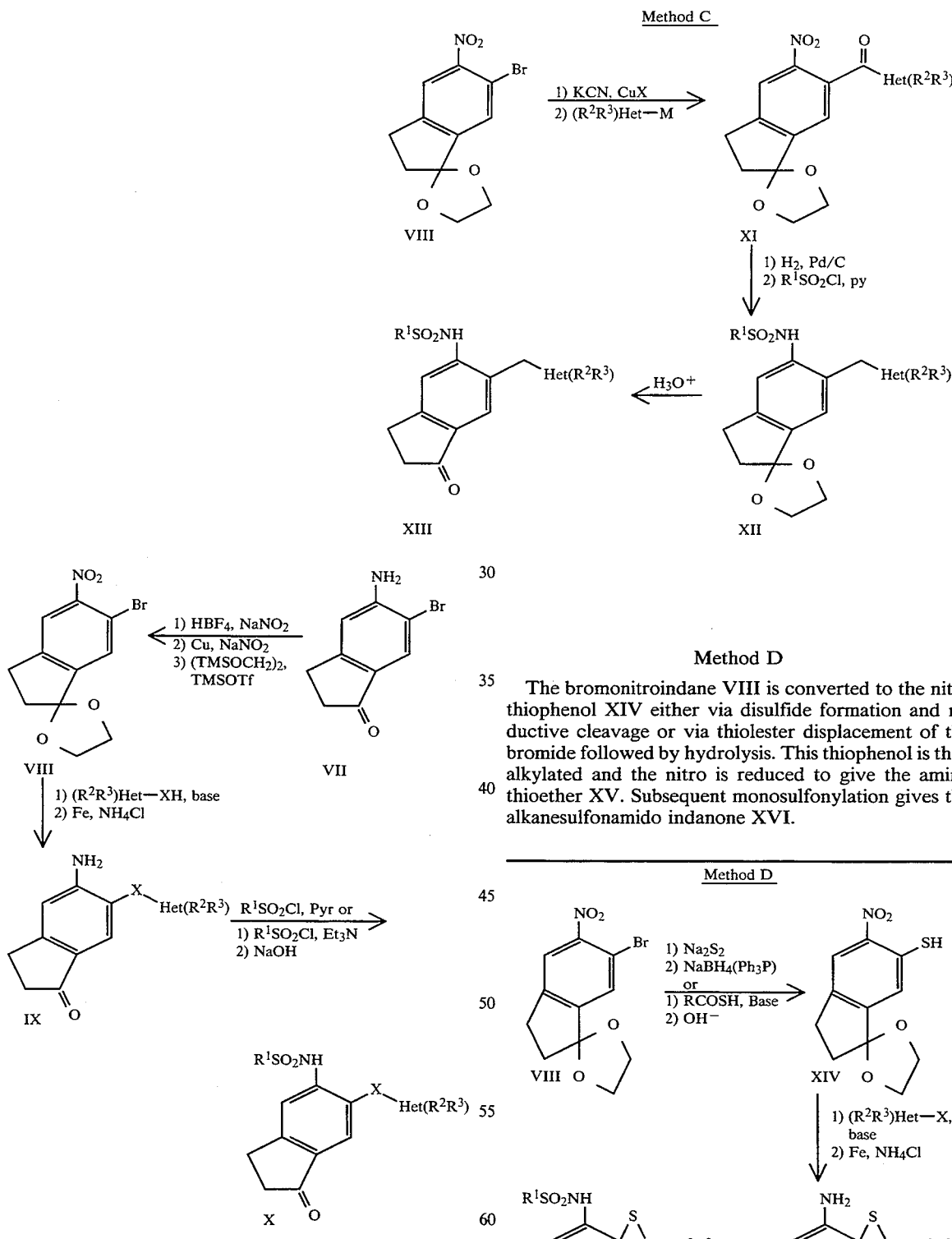

Method C

The bromo nitro indane VIII is converted to the ketone XI by cyanide displacement of the bromide followed by addition of an organometallic reagent such as a Grignard reagent onto the resulting nitrile and subsequent hydrolysis. Reduction and sulfonylation provides

Method D

The bromonitroindane VIII is converted to the nitro thiophenol XIV either via disulfide formation and reductive cleavage or via thiolester displacement of the bromide followed by hydrolysis. This thiophenol is then alkylated and the nitro is reduced to give the amino thioether XV. Subsequent monosulfonylation gives the alkanesulfonamido indanone XVI.

-continued

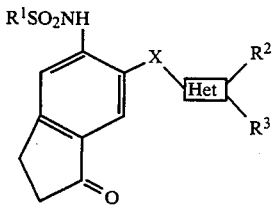

| Compound | X | R¹ | HETROCYCLE | R² | R³ |
|---|---|---|---|---|---|
| 1 | S | $CH_3$ | 2-Thienyl | — | — |
| 2 | S | $CH_3$ | 2-(1,3-)Diazinyl | 4-$CH_3$ | — |
| 3 | S | $CH_3$ | 2-Thiazolyl | — | — |
| 4 | S | $CH_3$ | 2-(1,3,4-)Thiadiazolyl | 5-$CH_3$ | — |
| 5 | O | $CH_3$ | 3-Thienyl | — | — |
| 6 | S | $CF_3$ | 2-thienyl | — | — |
| 7 | S | $CH_3$ | 2-Thiazolyl | 4-$CH_3$ | 5-$CH_3$ |
| 8 | S | $CH_3$ | 2-Imidazolyl | N—$CH_3$ | — |
| 9 | $CH_2$ | $CF_3$ | 2-Thiazolyl | 4-Cl | — |
| 10 | S | $CH_2CH_3$ | 3-Furyl | 2-$CH_3$ | — |
| 11 | S | $CH(CH_3)_2$ | 2-(1,3,4-)Thiadiazolyl | 5-$SCH_3$ | — |
| 12 | S | $CH_3$ | 2-(1,2,4-)Triazolyl | 1-$CH_3$ | 5-$CH_3$ |
| 13 | S | $CH_3$ | 4-(1,2,3-)Triazolyl | 1-$CH_3$ | — |
| 14 | O | $CH_3$ | 4-Isothiazolyl | — | — |
| 15 | O | $CF_3$ | 2-Thiazolyl | — | — |
| 16 | $CH_2$ | $CH_3$ | 2-Oxazolyl | — | — |
| 17 | O | $CH_3$ | 5-Thiazolyl | — | — |
| 18 | S | $CH_3$ | 5-Isothiazolyl | 3-$CH_3$ | — |
| 19 | O | $CH_3$ | 3-Isothiazolyl | — | — |
| 20 | S | $CH_3$ | 4-Isothiazolyl | 3-$CH_3$ | — |
| 21 | O | $CH_3$ | 4-(1,2,3-)Thiadiazolyl | — | — |
| 22 | S | $CH_3$ | 4-(1,2,5-)Thiadiazolyl | — | — |
| 23 | S | $CF_3$ | 3-Isoxazolyl | — | — |
| 24 | S | $CH_2CH_3$ | 5-(1,2,3-)Thiadiazolyl | — | — |
| 25 | S | $CH_3$ | 2-(1,3,4-)Oxadiazolyl | — | — |
| 26 | S | $CF_3$ | 3-(1,2,4-)Thiadiazolyl | 5-$CH_3$ | — |

Using the methods A-D above, and the methodology described in Example 3, Compounds 1, 2, and 4 were prepared.

EXAMPLES 1 (COMPOUND 1)

5-Methanesulfonamido-6-(2,-thienylthio)-1-indanone

Cal'd for Analysis C, 49.54; H, 3.86; N, 4.13 Found: C, 49.37; H, 3.79; N, 3.97

EXAMPLES 2 (COMPOUND 2)

5-Methanesulfonamido-6-(2-(4-methyl-1,3-diazinylthio))-1-indanone

High resolution mass spectrum (FAB): MH+ found at 350.06,330 calculated 3,50.06,330

EXAMPLES 3 (COMPOUND 3)

5-Methanesulfonamido-6-(2-thiazolylthio)-1-indanone, sodium salt

Step 1: 5-Acetylaminoindane

To a solution of 5-aminoindane (10.0 g, 7.5 mmol) in $CH_2Cl_2$ (100 mL) was added dropwise acetic anhydride (9.2 g, 9.0 mmol) over a period of 1.5 min. After further stirring for 30 min, the mixture was quenched with 1M aqueous NaOH (100 mL). The $CH_2Cd_2$ layer was separated, washed successively with 1M aqueous HCl, brine, and was then dried over anhydrous $MgSO_4$ and concentrated in vacuo. Chromatography over silica gel, eluting with ethyl acetate:hexanes (1:1) afforded 12.2 g (85%) of the title compound as a light brown powder.

¹H NMR ($CDCl_3$): δ7.44 (1H, s), 7.12 (3H, three overlapping s), 2.88 (4H, m), 2.15 (3H, s), 2.06 (2H, m).

Step 2: 5-Acetylamino-6-bromoindane

To a solution of 5-acetylaminoindane (53.0 g, 0.30 mmol) in glacial acetic acid (1 L) at 10° C. was added dropwise over a period of 1 h a solution of bromine (19.0 mL, 0.37 mmol). The mixture was further stirred at 10° C. for 15 min, and was then diluted with water until no more precipitate formed. The precipitate was collected, washed with water and dried under vacuum to give 61 g (80%) of the title compound.

¹H NMR ($CDCl_3$): δ8.14 (1H, s), 7.50 (1H, s), 7.38 (1H, s), 2.88 (4H, m), 2.20 (3H, s), 2.08 (2H, m).

Step 3: 5-Acetylamino-6-bromo-1-indanone

To a solution of 5-acetylamino-6-bromoindane (43.0 g, 0.17 mmol) in glacial acetic acid (400 ml) at 50°–55° C. was added dropwise a solution of chromium trioxide (70.0 g, 0.7 mmol) in 50% aqueous acetic acid (400 mL) over a period of 30 min. After further stirring for 15 min, the mixture was cooled to 0° C. and quenched with 2-propanol (100 mL). Solvent was removed in vacuo. The residue was diluted with water (1 L) and extracted with ethyl acetate (2×500 mL). The combined ethyl acetate layer was washed with 0.5M aqueous NaOH (1 L), brine, dried over anhydrous $MgSO_4$ and concentrated to give 36 g (80%) of the title compound as a light brown solid which was contaminated with about 10% of 5-bromo-6-acetylamino-1-indanone.

¹H NMR ($CDCl_3$): δ8.60 (1H, s), 7.98 (1H, s), 7.90 (1H, s), 3.10 (2H, t), 2.70 (2H, t), 2.30 (3H, s).

Step 4: 5-Amino-6-bromo-1-indanone

A mixture of 5-acetylamino-6-bromo-1-indanone (36.0 g, 0.13 mmol) and 6M aqueous hydrochloric acid (800 mL) was refluxed for 1 h. The homogenous solution was then cooled to 0° C. and adjusted to pH 8 with 10M aqueous NaOH (~480 mL). The precipitate formed was collected, washed with water and dried under vacuum to afford 30.0 g (quantitative) of the title compound as a light brown powder.

¹H NMR (acetone-d6): δ7.65 (1H, s), 6.90 (1H, s), 5.80 (2H, br s), 2.95 (2H, t), 2.50 (2H, t).

Step 5: 5-Nitro-6-bromo-1-indanone

To a suspension of 5-amino-6-bromo-1-indanone (30.0 g, 0.13 mmol) in 20% aqueous fluoroboric acid (120 mL) at 0° C. was added dropwise 4M aqueous $NaNO_2$ (50 mL, 0.20 mmol) over a period of 30 min. The mixture was stirred for 30 min after completion of addition. The resulting foamy suspension was added portionwise to a vigorously stirred mixture of copper powder (40 g, 0.62 mmol) and sodium nitrite (120 g, 1.74 mmol)in water (240 mL) at room temperature over a period of 15 min. During the addition, excessive foaming was broken up by the addition of small amounts of diethyl ether. After further stirring for 30 min, the mixture was filtered through celite, washed with ethyl acetate (5×300 mL). The ethyl acetate layer was separated, washed with brine, dried over anhydrous $MgSO_4$ and concentrated in vacuo. Chromatography over silica gel, eluting with $CH_2Cl_2$,yielded 17.5 g (51%) of the title compound as a pale yellow solid.

¹H NMR ($CDCl_3$): δ8.10 (1H, s), 7.85 (1H, s), 3.20 (2H, t), 2.85 (2H, t); mass spectrum (DCI, $CH_4$) m/e 256 (M++H).

Step 6: 5-Nitro-6-bromo-1-indanone ethylene acetal

To a suspension of 5-nitro-6-bromo-1-indanone (11.0 g, 43 mmol) and bis(trimethylsilyloxy)ethane (22.0 mL, 90 mmol) in CH$_2$Cl$_2$ (90 mL) at room temperature was added trimethylsilyltrifluoromethanesulfonate (100 μL). The mixture was stirred for 2 h and the homogeneous solution was quenched with saturated aqueous NaHCO$_3$ (100 mL). The CH$_2$Cl$_2$ layer was separated, washed with brine, dried over anhydrous MgSO$_4$ and concentrated in vacuo. Chromatography over silica gel, eluting with ethyl acetate:hexanes (2:5), furnished 10.2 g (79%) of the title compound as a pale yellow solid.

$^1$H NMR (CDCl$_3$): δ7.70 (1H, s), 7.68 (1H, s), 4.15 (4H, m), 2.98 (2H, t), 2.38 (2H, t).

Step 7: 5-Nitro-6-(2thiazolylthio)-1-indanone ethylene acetal

The bromide from Step 6 (410 mg, 1.37 mmol) and 2-mercaptothiazole (200 mg, 1.7 mmol) were mixed together in pyridine (3 mL) at room temperature. Aqueous KOH (8M, 213 μL, 1.7 mmol) was added and the resulting mixture was heated with an oil bath at 80° C. for 3 h, then at 100° C. for 1.5 h and finally 75° C. for 16 h. After cooling to room temperature the mixture was diluted and EtOAc and washed with water. The organic layer was dried over MgSO$_4$ and concentrated in vacuo. Purification by flash chromatography on silica gel (from 5% acetone in 2:1 CH$_2$Cl$_2$-hexanes to 10% acetone in CH$_2$Cl$_2$) yielded 280 mg of the title compound.

$^1$H NMR (CDCl$_3$): δ8.50 (1H, s), 7.99 (1H, d), 7.58 (1H, d), 7.11 (1H, d), 4.05–3.90 (4H, m), 2.97 (2H, t), 2.32 (2H, t).

Step 8: 5-Amino-6-(2-thiazolylthio)-1-indanone

Iron powder (265 mg, 4.7 mmol), ammonium chloride (35 mg, 0.65 mmol) and the nitroindane from Step 7 (275 mg, 0.82 mmol) were mixed together in ethanol (5 ml) and water (2.5 mL). The mixture was refluxed for 1 h and then filtered through celite, washing the cake with EtOAc. The volatile, s were removed in vacuo and the residue was dissolved in EtOAc:CH$_2$Cl$_2$ (3:1), washed with brine and dried over MgSO$_4$. Evaporation of the solvent left a residue that was purified by flash chromatography on silica gel (EtOAc:toluene:CH$_2$Cl$_2$ from 30:50:20 to 1:1:1) to give 150 mg of the title compound.

$^1$H NMR (CDCl$_3$): δ8.03 (1H, s), 7.67 (1H, d), 7.20 (1H, d), 6.78 (1H, d), 5.05 (2H, br s), 3.05 (2H, m), 2.67 (2H, m).

Step 9: 5-Bis(methanesulfonyl)amino-6-(2-thiazolylthio)-1-indanone

Methanesulfonyl chloride (710 μL, 9.15 mmol) and pyridine (740 μL, 9.15 mmol) were added to a solution of the aminoindanone from Step 8 in CH$_2$Cl$_2$ (5 mL). After stirring overnight at room temperature, Et$_3$N (400 μL, 2.8 mmol) and methanesulfonyl chloride (220 μL, 2.8 mmol) were added. The mixture was stirred 4 h at room temperature. Water and CH$_2$Cl$_2$ were added, the aqueous phase was extracted with CH$_2$Cl$_2$ and the combined organic phase was washed with 0.1M aqueous citric acid, dried over MgSO$_4$ and concentrated in vacuo. The crude residue was purified by flash chromatography on silica gel (20% EtOAc in CHCl$_2$) to give 175 mg of the title compound.

$^1$H NMR (CDCl$_3$): δ7.96 (1H, s), 7.79 (1H, d), 7.58 (1H, s), 7.39 (1H, d), 3.55 (6H, s), 3.21 (2H, m), 2.77 (2H, m).

Step 10: 5-Methanesulfonamido-6-(2-thiazolylthio),1-indanone)

The bismethanesulfonamide from Step 9 (175 mg, 0.42 mmol) was dissolved in THF (4 mL) and methanol (500 μL) at room temperature. Aqueous NaOH (2.0M, 630 μL, 1.25 mmol) was added and the mixture stirred for 30 min. Saturated aqueous ammonium chloride was added and the mixture was extracted twice with EtOAc. The organic layer was dried over MgSO$_4$ and concentrated in vacuo. The crude was purified by flash chromatography (EtOAc:CH$_2$Cl$_2$:2-propanol, from 15:83:2 to 25:70:5) to give 96 mg of the title compound.

$^1$H NMR (CDCl$_3$): δ8.91 (1H, br s), 8.11 (1H, s), 7.88 (1H, s), 7.71 (1H, d), 7.32 (1H, d), 3.18 (2H, m), 3.07 (3H, s), 2.72 (2H, m).

Step 11: 5-Methanesulfonamido-6-(2-thiazolylthio)-1-indanone, sodium salt

The methanesulfonamide of Step 10 (96 mg, 0.28 mmol) was dissolved in ethanol (1 mL).Aqueous NaOH (1.0M, 280 μL, 0.28 mmol) was added followed by water (5 mL). The mixture was concentrated in vacuo and the aqueous residue was freeze-dried overnight to give 100 mg of the title compound.

High Resolution. Mass (FAB) MH+ found at 362.99078 MH+ calculated at 362.9907775

EXAMPLES 4 (COMPOUND 4)

5-Methanesulfonamido-6-(2-(5-methyl-1,3,4-thiadiazoylthio))-1 -indanone

[M+Na]+ =378

What is claimed is:

1. A compound of formula I

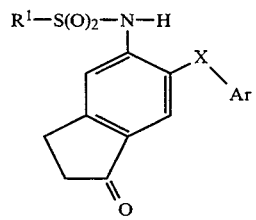

or a pharmaceutically acceptable salt thereof wherein:
R$^1$ is selected from the group consisting of
  (a) C$_{1-7}$alkyl, and
  (b) mono-, di-, tri-, tetra- and per-substituted C$_{1-7}$alkyl, wherein the substitutent is fluoro;
X is O, S, or —CH$_2$—;
Ar is a mono or disubstituted aromatic ring, said ring selected from
  (a) a ring of 5 atoms containing one O, S or N atom and optionally, 1, 2 or 3 additional N atoms; and
  (b) a ring of 6 atoms containing 3 or 4 nitrogen atoms;
wherein the substituents are independently selected from
  (a) hydrogen,
  (b) C$_{1-7}$alkyl,
  (c) F, Cl, Br, and I,
  (d) OCH$_3$,
  (e) SCH$_3$,
  (f) CF$_3$,
  (g) COCH$_3$ and
  (h) S(O)$_2$CH$_3$.

2. A compound of formula I

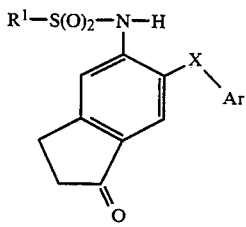

or a pharmaceutically acceptable salt thereof wherein:
R$^1$ is selected from the group consisting of
 (a) C$_{1-7}$alkyl, and
 (b) mono-, di-, tri-, tetra- and per-substituted C$_{1-7}$alkyl, wherein the substitutent is fluoro;
X is O, S, or —CH$_2$—;
wherein:
Ar is a mono or di-substituted aromatic group wherein the aromatic group is selected from the group consisting of
 (1) furanyl,
 (2) triazinyl and tetrazinyl,
 (3) imidazolyl,
 (4) isooxazolyl,
 (5) isothiazolyl,
 (6) oxadiazolyl,
 (7) oxazolyl,
 (8) pyrazolyl,
 (9) pyrrolyl,
 (10) thiadiazolyl,
 (11) thiazolyl,
 (12) thienyl,
 (13) triazolyl, and
 (14) tetrazolyl,
wherein the substituents are independently selected from
 (a) hydrogen,
 (b) C$_{1-7}$alkyl,
 (c) F, Cl, Br, and I,
 (d) OCH$_3$,
 (e) SCH$_3$,
 (f) CF$_3$,
 (g) COCH$_3$, and
 (h) S(O)$_2$CH$_3$.

3. A compound according to claim 2 wherein
R$^1$ is selected from the group consisting of
 (a) methyl, ethyl, propyl and butyl,
 (b) mono, di or tri substituted methyl, ethyl, propyl or butyl, wherein the substituent is fluoro;
X is O,
Ar is a mono or di substituted aromatic group wherein the aromatic group is selected from the group consisting of
 (1) isooxazolyl,
 (2) isothiazolyl,
 (3) oxadiazolyl,
 (4) oxazolyl,
 (5) thiadiazolyl, and
 (6) thiazolyl,
wherein the substituents are independently selected from
 (a) hydrogen,
 (b) C$_{1-3}$alkyl,
 (c) F or Cl,
 (d) OCH$_3$,
 (e) SCH$_3$, and
 (f) CF$_3$.

4. A compound according to claim 3 wherein
R$^1$ is selected from the group consisting of
 (a) methyl, ethyl or propyl, and
 (b) mono, di or tri substituted methyl, ethyl or propyl, wherein the substituent is fluoro;
X is O;
Ar is a mono or di substituted aromatic group wherein the aromatic group is selected from the group consisting of
 (1) 3-isooxazolyl,
 (2) 4-isooxazolyl,
 (3) 5-isooxazolyl,
 (4) 3-isothiazolyl,
 (5) 4-isothiazolyl,
 (6) 5-isothiazolyl,
 (7) 2-oxazolyl,
 (8) 4-oxazolyl,
 (9) 5-oxazolyl,
 (10) 2-thiazolyl,
 (11) 4-thiazolyl,
 (12) 5-thiazolyl,
 (13) 1,2,3-thiadiazol-4-yl,
 (14) 1,2,3-thiadiazol-5-yl,
 (15) 1,2,4-thiadiazol-3-yl,
 (16) 1,2,4-thiadiazol-5-yl,
 (17) 1,3,4-thiadiazol-2-yl,
 (18) 1,2,5-thiadiazol-3-yl,
 (19) 1,2,3-oxadiazol-4-yl,
 (20) 1,2,3-oxadiazol-5-yl,
 (21) 1,2,4-oxadiazol-3-yl,
 (22) 1,2,4-oxadiazol-5-yl,
 (23) 1,3,4-oxadiazol-2-yl, and
 (24) 1,2,5-oxadiazol-3-yl,
wherein the substituents are independently selected from
 (a) hydrogen,
 (b) methyl, ethyl or propyl,
 (c) F or Cl, and
 (d) OCH$_3$.

5. A compound according to claim 4 wherein
R$^1$ is methyl;
X is O;
Ar is a mono or di substituted aromatic group wherein the aromatic group is selected from the group consisting of
 (1) 3-isothiazolyl,
 (2) 4-isothiazolyl,
 (3) 5-isothiazolyl,
 (4) 2-oxazolyl,
 (5) 4-oxazolyl,
 (6) 5-oxazolyl,
 (7) 2-thiazolyl,
 (8) 4-thiazolyl, and
 (9) 5-thiazolyl,
wherein the substituents are independently selected from
 (a) hydrogen,
 (b) methyl or ethyl,
 (c) F or Cl, and
 (d) OCH$_3$.

6. A compound according to claim 2 wherein
R$^1$ is selected from the group consisting of
 (a) methyl, ethyl, propyl and butyl,
 (b) mono, di or tri substituted methyl, ethyl, propyl or butyl, wherein the substituent is fluoro;
X is CH$_2$, Ar is a mono or di substituted aromatic group wherein the aromatic group is selected from the group consisting of
(1) isooxazolyl,
(2) isothiazolyl,
(3) oxadiazolyl,
(4) oxazolyl,
(5) thiadiazolyl, and
(6) thiazolyl,
wherein the substituents are independently selected from
(a) hydrogen,
(b) $C_{1-3}$alkyl,
(c) F or Cl,
(d) $OCH_3$,
(e) $SCH_3$, and
(f) $CF_3$.

7. A compound according to claim 6 wherein
$R^1$ is selected from the group consisting of
(a) methyl, ethyl or propyl, and
(b) mono, di or tri substituted methyl, ethyl or propyl, wherein the substituent is Fluoro;
X is $CH_2$;
Ar is a mono or di substituted aromatic group wherein the aromatic group is selected from the group consisting of
(1) 3-isooxazolyl,
(2) 4-isooxazolyl,
(3) 5-isooxazolyl,
(4) 3-isothiazolyl,
(5) 4-isothiazolyl,
(6) 5-isothiazolyl,
(7) 2-oxazolyl,
(8) 4-oxazolyl,
(9) 5-oxazolyl,
(10) 2-thiazolyl,
(11) 4-thiazolyl,
(12) 5-thiazolyl,
(13) 1,2,3-thiadiazol-4-yl,
(14) 1,2,3-thiadiazol-5-yl,
(15) 1,2,4-thiadiazol-3-yl,
(16) 1,2,4-thiadiazol-5-yl,
(17) 1,3,4-thiadiazol-2-yl,
(18) 1,2,5-thiadiazol-3-yl,
(19) 1,2,3-oxadiazol-4-yl,
(20) 1,2,3-oxadiazol-5-yl,
(21) 1,2,4-oxadiazol-3-yl,
(22) 1,2,4-oxadiazol-5-yl,
(23) 1,3,4-oxadiazol-2-yl, and
(24) 1,2,5-oxadiazol-3-yl,
wherein the substituents are independently selected from
(a) hydrogen,
(b) methyl, ethyl or propyl,
(c) F or Cl, and
(d) $OCH_3$.

8. A compound according to claim 7 wherein
$R^1$ is methyl;
X is $CH_2$;
Ar is a mono or di substituted aromatic group wherein the aromatic group is selected from the group consisting of
(1) 3-isothiazolyl,
(2) 4-isothiazolyl,
(3) 5-isothiazolyl,
(4) 2-oxazolyl,
(5) 4-oxazolyl,
(6) 5-oxazolyl,
(7) 2-thiazolyl,
(8) 4-thiazolyl, and
(9) 5-thiazolyl,
wherein the substituents are independently selected from
(a) hydrogen,
(b) methyl or ethyl,
(c) F or Cl, and
(d) $OCH_3$.

9. A compound according to claim 2 wherein
$R^1$ is selected from the group consisting of
(a) methyl, ethyl or propyl, and
(b) mono, di or tri substituted methyl, ethyl, propyl or butyl, wherein the substituent is fluoro;
X is S;
Ar is a mono or di substituted aromatic group wherein the aromatic group is selected from the group consisting of
(1) isooxazolyl,
(2) isothiazolyl,
(3) oxadiazolyl,
(4) oxazolyl,
(5) thiadiazolyl, and
(6) thiazolyl,
wherein the substituents are independently selected from
(a) hydrogen,
(b) $C_{1-3}$alkyl,
(c) F or Cl,
(d) $OCH_3$,
(e) $SCH_3$, and
(f) $CF_3$.

10. A compound according to claim 9 wherein
$R^1$ is selected from the group consisting of
(a) methyl, ethyl or propyl, and
(b) mono, di or tri substituted methyl, ethyl or propyl, wherein the substituent is Fluoro;
X is S;
Ar is a mono or di substituted aromatic group wherein the aromatic group is selected from the group consisting of
(1) 3-isooxazolyl,
(2) 4-isooxazolyl,
(3) 5-isooxazolyl,
(4) 3-isothiazolyl,
(5) 4-isothiazolyl,
(6) 5-isothiazolyl,
(7) 2-oxazolyl,
(8) 4-oxazolyl,
(9) 5-oxazolyl,
(10) 2-thiazolyl,
(11) 4-thiazolyl,
(12) 5-thiazolyl,
(13) 1,2,3-thiadiazol-4-yl,
(14) 1,2,3-thiadiazol-5-yl,
(15) 1,2,4-thiadiazol-3-yl,
(16) 1,2,4-thiadiazol-5-yl,
(17) 1,3,4-thiadiazol-2-yl,
(18) 1,2,5-thiadiazol-3-yl,
(19) 1,2,3-oxadiazol-4-yl,
(20) 1,2,3-oxadiazol-5-yl,
(21) 1,2,4-oxadiazol-3-yl,
(22) 1,2,4-oxadiazol-5-yl,
(23) 1,3,4-oxadiazol-2-yl, and
(24) 1,2,5-oxadiazol-3-yl,
wherein the substituents are independently selected from
(a) hydrogen, (b) methyl, ethyl or propyl,
(c) F or Cl, and
(d) OCH$_3$.

11. A compound according to claim 10 wherein R$^1$ is methyl;
X is S;
Ar is a mono or di substituted aromatic group wherein the aromatic group is selected from the group consisting of
(1) 3-isothiazolyl,
(2) 4-isothiazolyl,
(3) 5-isothiazolyl,
(4) 2-oxazolyl,
(5) 4-oxazolyl,
(6) 5-oxazolyl,
(7) 2-thiazolyl,
(8) 4-thiazolyl,
(9) 5-thiazolyl,
wherein the substituents are independently selected from
(a) hydrogen,
(b) methyl or ethyl,
(c) F or Cl, and
(d) OCH$_3$.

12. A compound of formula

[Structures showing CH$_3$—S(O)$_2$—N—H and CH$_3$—S(O)$_2$—N—Z$^+$ variants with Ar substituent]

Z is pharmaceutically acceptable monovalent counterion,
Ar is a mono or di substituted aromatic group wherein the aromatic group is selected from the group consisting of
(1) 3-isothiazolyl,
(2) 4-isothiazolyl,
(3) 5-isothiazolyl,
(4) 2-oxazolyl,
(5) 4-oxazolyl,
(6) 5-oxazolyl,
(7) 2-thiazolyl,
(8) 4-thiazolyl, and
(9) 5-thiazolyl,
wherein the substituents are independently selected from
(a) hydrogen,
(b) methyl or ethyl,
(c) F or Cl, and
(d) OCH$_3$.

13. A compound according to claim 12 selected from the group consisting of

[Structures 1, 2, 3, 4 showing indanone derivatives with CH$_3$—S(O)$_2$—N—H groups and various heterocyclic substituents]

or a pharmaceutically acceptable salt thereof.

14. A pharmaceutical compositions of inhibiting cyclooxygenase comprising a pharmaceutically acceptable carrier and a non-toxic therapeutically effective amount of compound according to claim 2.

15. A pharmaceutical compositions of inhibiting cyclooxygenase-2 comprising a pharmaceutically acceptable carrier and a non-toxic therapeutically effective amount of compound according to claim 1.

16. A method of inhibiting cyclooxygenase comprising:
administration to a patient in need of such inhibition of a non-toxic therapeutically effective amount of a compound according to claim 1.

17. A method of inhibiting cyclooxygenase-2 comprising:
administration to a patient in need of such treatment of a non-toxic therapeutically effective amount of a compound according to claim 2.

18. A pharmaceutical composition for the treatment of cyclooxygenase-2 mediated disease comprising a non-toxic therapeutically effective amount of compound according to claim 2 and at least one or more ingredients selected from a pain reliever including acetaminophen or phenacetin; a potentiator including caffeine; an H2-antagonist, aluminum or magnesium hydroxide, simethicone, a decongestant including phenylephrine, phenylpropanolamine, pseudopheorine, oxymetazoline, ephinephrine, naphazoline, xylometazoline, propylhexedrine, or levo-desoxyephedrine; an antitussive including codeine, hydrocodone, caramiphen, carbetapentane, or dextramethorphan; a diuretic; and a sedating or non-sedating antihistamine.

* * * * *